United States Patent [19]

Dufresne et al.

[11] Patent Number: 4,803,986

[45] Date of Patent: Feb. 14, 1989

[54] ERGONOMETRIC TRANSCUTANEOUS ELECTRICAL NERVE STIMULATOR

[75] Inventors: Joel R. Dufresne; Alan P. Dieken, both of St. Paul, Minn.; John E. Studer, Jr., Madison, N.J.

[73] Assignee: Minnesota Mining and Manufacturing Company, St. Paul, Minn.

[21] Appl. No.: 42,291

[22] Filed: Apr. 24, 1987

[51] Int. Cl.[4] .............................................. A61N 1/00
[52] U.S. Cl. .................................. 128/385; 128/419 R
[58] Field of Search .................... 128/379, 385, 419 P, 128/419 D, 419 R, 421, 422, 423, 802

[56] References Cited

U.S. PATENT DOCUMENTS

| Re. 30,028 | 6/1979 | Purdy et al. | 128/419 P |
|---|---|---|---|
| 447,857 | 3/1891 | Williams | 128/385 |
| 3,025,858 | 3/1962 | Browner | 128/422 |
| 3,718,142 | 2/1973 | Molier | 128/419 P |
| 4,033,356 | 7/1977 | Hara | 128/422 |
| 4,542,753 | 9/1985 | Brenman et al. | 128/421 |

Primary Examiner—Ruth Smith
Attorney, Agent, or Firm—Donald M. Sell; William D. Bauer

[57] ABSTRACT

An ergonometric transcutaneous electrical nerve stimulator especially designed for dysmenorrhea and low back pain. The ergonometric factors include a housing containing the electrical circuit, the housing being of a generally flattened disk shape with well rounded edges. A first power switch is located on a side edge of the housing, and one or more rocker switches controlling the amplitude of the current stimulation pulses to be supplied by one or more channels from the stimulator are mounted on a side edge of the housing. The housing of the stimulator has one or more attachment points on the side edge of the housing to allow for connection of the housing to a body or garment strap.

10 Claims, 3 Drawing Sheets

ERGONOMETRIC TRANSCUTANEOUS ELECTRICAL NERVE STIMULATOR

BACKGROUND OF THE INVENTION

The present invention relates generally to transcutaneous electrical nerve stimulators and more particularly to transcutaneous electrical nerve stimulators designed to alleviate chronic pain.

Transcutaneous electrical nerve stimulators are typically utilized to mask pain signals of a human body before they reach the brain giving the subject apparent relief from the pain. Electrical pulses are delivered to the skin of the subject by one or more electrodes. The subject typically can control the transcutaneous electrical nerve stimulator through adjustment of its output current of the pulses. The transcutaneous electrical nerve stimulator may have a plurality of outputs, e.g., two, channels, each simultaneously and independently providing electrical stimulation pulses.

One common use for a transcutaneous electrical nerve stimulator is for chronic pain situations such as those related to menstrual pain, dysmenorrhea and for lower back pain.

Prior transcutaneous electrical nerve stimulators have used rectangular cases with relatively sharp corners.

For menstrual pain and lower back pain applications, a transcutaneous electrical nerve stimulator is desirably worn on the body of the person in a relatively inconspicuous location, consistent with ready, comfortable, and reliable access to its operable controls.

Transcutaneous electrical nerve stimulators with rectangular case design have sharp corners which when placed under pressure next to the body, can cause user discomfort by marking, scratching or abraiding the skin. Yet, pain and discomfort are exactly what the stimulator should help prevent. Further, user controls are often either confusing in their location or are not easily operable with one hand. Also, little consideration has previously been given to the ease of attachment of the transcutaneous electrical nerve stimulator to the body.

SUMMARY OF THE INVENTION

The present invention provides a transcutaneous electrical nerve stimulator having an electrical circuit for generating a predetermined set of electrical stimulus signals adapted to be applied to a body. A housing contains the electrical circuit. The housing is of a generally flattened disk shape with well rounded edges. A first switch is mounted on a side edge of the housing and coupled to the electrical circuit controlling the intensity of the electrical stimulus signal. A second switch is mounted on a side edge of the housing and coupled to the electrical circuit controlling power to the electrical circuit. Preferably the housing has a first attachment point at one side edge and a second attachment point at an opposite side edge.

In a preferred embodiment, the transcutaneous electrical nerve stimulator has the first switch being a rocker switch which is pushed by an operator toward the first attachment point to increase the amplitude of the electrical stimulus signal and which operates to decrease the amplitude of the electrical stimulus signal when pushed by the operator toward the second attachment point.

In another embodiment of the present invention, the transcutaneous electrical nerve stimulator has an electrical circuit having a plurality of independent stimulation channels each generating a predetermined set of electrical stimulus signals. The first switch controls the electrical stimulus signal for one of the plurality of independent stimulation channels and the stimulator further has at least one additional rocker switch mounted on an edge of the housing and coupled to the electrical circuit for controlling the amplitude of the electrical stimulus signal of another of the plurality of stimulation channels in a manner similar to the manner in which the first rocker switch controls the amplitude of its associated one of said set of electrical stimulus signals.

The unique shape of the transcutaneous electrical nerve stimulator of the present invention is advantageous for immediate placement next to the body without sharp edges to scratch, rub or abraid the skin. The flattened disk shape provides for unobtrusive wearability on the body, particularly the female body. The slightly convex surfaces of the flattened disk shape allow internal placement of a rigid printed circuit board containing electrical components. Components with the highest profile are mounted toward the center of the board, and those of a lower profile are located towards the circumference of the board. This arrangement provides a more compact size and, even more importantly, a much smaller perceived size by the user than with prior rectangular case designs.

The optimum user control interface has operable switches positioned on the side edges of the flattened disk. The force required to operate the controls on the side edges may be easily balanced by the forces applied by opposing fingers of the same hand. This approach minimizes discomfort by obviating the need to push the case (housing) into the body when operating the controls. Rocker switches are utilized to minimize the number of switches required, facilitate the user's location of controls under clothing, and to increase the ease of output amplitude adjustment. An increase in amplitude requires simply a push of the rocker mechanism towards the top of the case (when hung properly) and vice versa for a decrease in stimulation amplitude.

The transcutaneous electrical nerve stimulator has advantageously designed and located attachment points enabling the stimulator to be conveniently attached to the body. For example, the stimulator may be hung from the strap of bras or other undergarments, from a belt at the waist, or "pendant style" from straps fitted around the neck.

BRIEF DESCRIPTION OF DRAWINGS

The foregoing advantages, operation, and construction of the present invention will become more readily apparent from the following description and accompanying drawings in which.

DETAILED DESCRIPTION OF THE PREFERRED EMBODIMENTS

Figure 1:
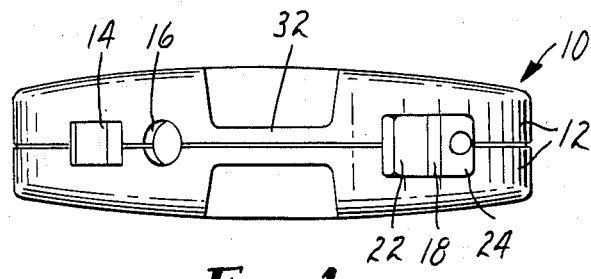
FIG. 1 is a top view of a transcutaneous electrical nerve stimulator of the present invention.
Figure 2:
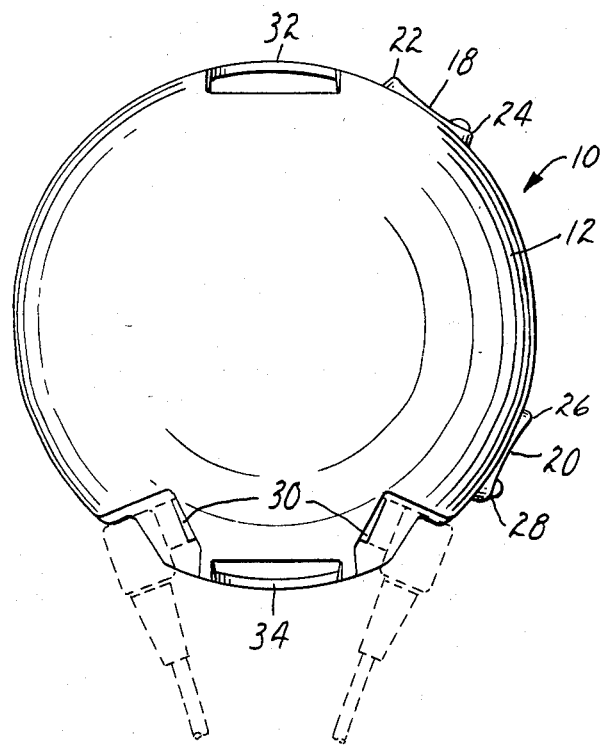
FIG. 2 is a front view of the transcutaneous electrical nerve stimulator of the present invention.

FIGS. 1 and 2 show the top and the front views of a transcutaneous electrical nerve stimulator (TENS) 10. The stimulator 10 has a housing 12 which is of a generally flattened disk shape having well rounded edges. The flattened disk shape is of slightly elliptical dimension to aid in appearance and to facilitate a hanging-style attachment. At one location on the side edge of the housing 12 is mounted a power switch 14 which may be operator controlled to quickly turn on or off the power to the stimulator. An indicator light 16 is also provided, in a preferred embodiment, as an aid to showing the user that power is being supplied to the stimulator 10 and/or that battery power is nearly exhausted. In the preferred embodiment, the stimulator 10 has two output channels. The amplitude of the current pulses supplied by each output channel is controlled by rocker switches 18 and 20, respectively, each mounted on one side edge of the housing 12. Rocker switch 18 controls the current amplitude of the stimulation pulse to be delivered by channel 1 of the stimulator 10 while rocker switch 20 controls the current amplitude of the current stimulation pulse supplied by channel 2 of the stimulator 10. Preferably, rocker switches 18 and 20 are located on one lateral hemisphere of housing 12. Preferably the rocker switch 18 for channel 1 is positioned toward the top of the stimulator 10 while the rocker switch for channel 2 is located in the lower portion of stimulator 10. Rocker switch 18 rests in a neutral position when not being operated by the user. When rocker switch 18 is pushed at end 22, an increase in the current amplitude of the channel 1 stimulation pulse is accomplished. Conversely, pushing rocker switch 18 at end 24 operates to decrease the current amplitude of the channel 1 stimulation pulse. Similarly, rocker switch 20 when pushed at end 26 increases the current amplitude of the channel 2 stimulation pulse. Correpondingly, a push at end 28 decreases the current amplitude. Electrical jacks 30 are provided to individually allow connection of stimulation electrodes to the stimulator 10. A first attachment point 32 is provided on the housing 12 at the top of the stimulator 10. A second attachment point 34 is provided on a side edge of the housing 12 opposite the first attachment point 32. In a preferred embodiment, attachment points 32 and 34 are formed as an attachment bar mounted on housing 12 over a tapered depression in the housing thus forming an unobtrusive channel. A mounting strap may then be passed through said channel and secured to the body or to clothing.

Figure 3:
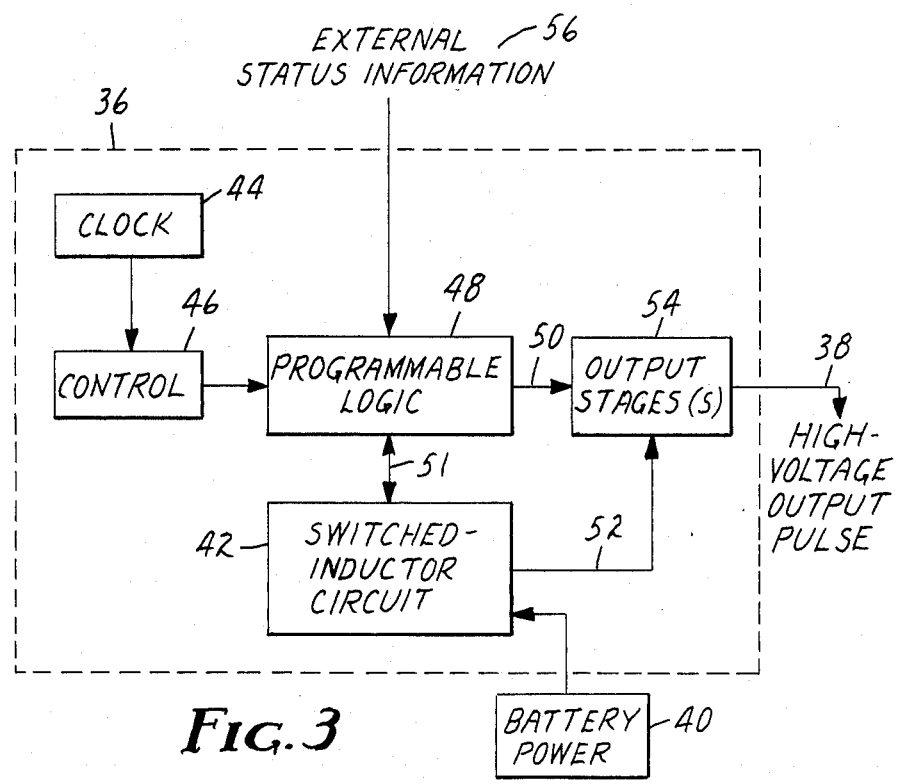
FIG. 3 is a block diagram of the internal electrical components of the transcutaneous electrical nerve stimulator of the present invention.

FIG. 3 illustrates a general block diagram of the electrical circuit 36 required to supply high voltage current output pulses 38 of the stimulator 10. Generally, battery power 40 is supplied to a switched inductor circuit 42. A clock 44 drives a control circuit 46 which in turn supplies a programmable logic block 48 which supplies switching signals 51 to switched inductor circuit 42 for generating a high-voltage signal 52 to be supplied to output stages 54. Programmable logic block 48 also supplies timing and amplitude information signals 50 to output stages 54 which then utilizes a high-voltage signal 52 to supply electrical stimulation signal 38. Programmable logic block 48 receives external status information 56 and conditionally supplies power to indicator light 16 on a periodic basis. Included in the external status information 56 is the condition of switches 14, 18 and 20 and the voltage level of the battery power supply. The block diagram of the electrical circuit 36 illustrated in FIG. 3 is general and of the generally perferred electrical circuit of the transcutaneous electrical nerve stimulator 10 of the present invention. It is to be recognized and understood that electrical circuits for use in transcutaneous electrical nerve stimulators are well known in the art. Any of the generally available electrical circuits could be utilized in the transcutaneous electrical nerve stimulator 10 of the present invention. The particular block diagram illustrated in FIG. 3 is supplied for convenience and no particular engineering skill should be required to obtain or design any one of a number of existing electrical circuits 36 which can be utilized in transcutaneous electrical nerve stimulators 10. The particular electrical circuit 36 illustrated in FIG. 3 is additionally described in copending U.S. patent application Ser. No. 042,166, filed Apr. 24, 1987 in the name of inventors Dufresne et al, entitled, Biological Tissue Stimulator With Time-Shared Logic Driving Output Timing and High-Voltage Step-up Circuit, assigned to the assignee of the present application, the contents of which application are hereby incorporated by reference.

The transcutaneous electrical nerve stimulator 10 shown and described uses a variety of technics to both improve wearability and to give a visual impression of small size and good asthetics. The significant radiusing of the outside edges of housing 12, the angled placement of jacks 30 and the spherically convex shaping of the front and rear surfaces of housing 12 contribute to the desired result. The placement on side edges of user control switches 14, 18 and 20 make them less conspicuous while making them easier to operate. The asymmetrical placement of power switch 14 as compared to amplitude switches 18 and 20 aids in their location and positive identification by the user even when the stimulator 10 is worn under clothing. The rocker switches 18 and 20 permit amplitude to be adjusted in steps. Depression of the rocker switches 18 and 20 toward the top of the housing 12 causes an increase in stimulation pulse 38 amplitude while depression toward the bottom of the housing 12 causes a decrease in pulse amplitude. When not actively depressed by the user, rocker switches 18 and 20 rest in a neutral position. Rocker switches 18 and 20 are provided with an electronic delay mechanism so that rocker switch depressions of less than 0.5 second only result in a single step change in amplitude. However, if the rocker switches 18 or 20 are continuously depressed, step changes will be generated at regular intervals (typically 0.5 seconds) until either stimulation amplitude has been decreased to zero or stimulation amplitude has reached its maximum allowable amplitude. In a preferred embodiment, a total of 64 steps in current amplitude are provided. These timing parameters are chosen to permit a precise setting of comfortable stimulation amplitudes by the user. Continuous depression of rocker switches 18 or 20 is generally used to rapidly reach the general region of comfortable current amplitudes, while subsequent discrete depressions are designed to provide single step amplitude corrections.

Rocker switches were chosen for switches 18 and 20 rather than individual increase and decrease buttons to simplify the user interface since only one switch (rather than two) needs to be located for each channel of operation. The side edge mounting of rocker switches 18 and 20 minimize the pressure against the skin. The pressure necessary to activate the side-mounted switches 18 and 20 by one finger is easily opposed by fingers of the same hand resting on the opposite side of the stimulator 10. Thus, the forces applied to the rocker switches 18 or 20 are not also directed at tender regions of the body such as the breasts or abdomen. Preferably, rocker switches 18 and 20 are designed to minimize their projection from the side of the housing 12 and, thus, reduce the chance for inadvertent amplitude adjustment as well as being selected for good tactile feedback.

Figure 4:
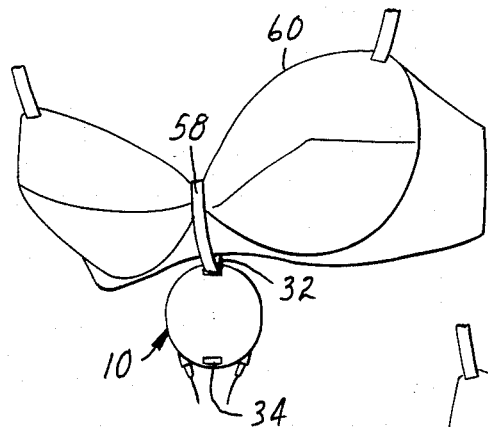
FIGS. 4 and 5 illustrates alternative bra strap attachment mechanisms for the transcutaneous electrical nerve stimulator of the present invention.
Figure 5:
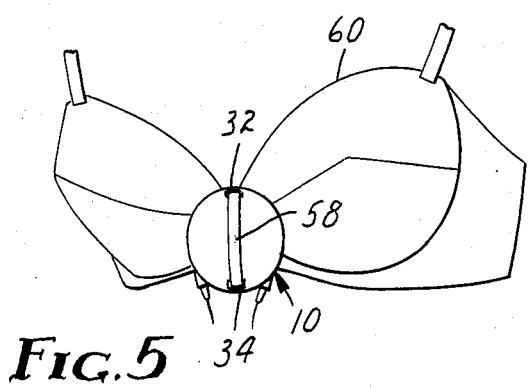

Housing 12 has two attachment points 32 and 34, top and bottom, respectively. These attachment points 32 and 34 consist of "channels" or depressions in the case over which a bar is mounted to the housing permitting the use of various ribbons or straps as attachment devices. These ribbon attachments may consist of a self-fastening material such as a hook and loop fastener or elastic materials. One of these attachment mechanisms is illustrated in FIG. 4. Here the stimulator 10 is hung from the first attachment point 32 by a strap 58 which passes around the center portion of a bra 60. An alternative bra attachment mechanism is illustrated in FIG. 5 in which the stimulator 10 is again held by a strap 58 passed around the central portion of a bra 60 but this time made more secure by having strap 58 pass through both top attachment point 32 and bottom attachment point 34.

Figure 6:
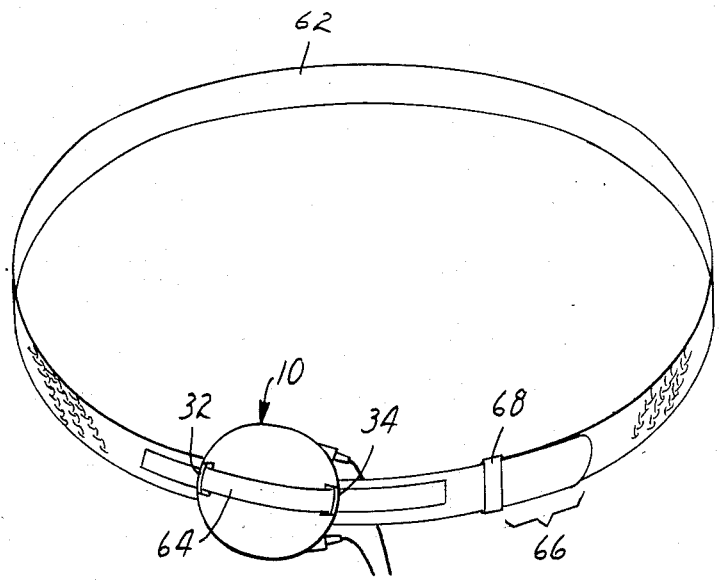
FIGS. 6 and 7 illustrate alternative waist belt attachment mechanisms for the transcutaneous electrical nerve stimulator of the present invention.
Figure 7:
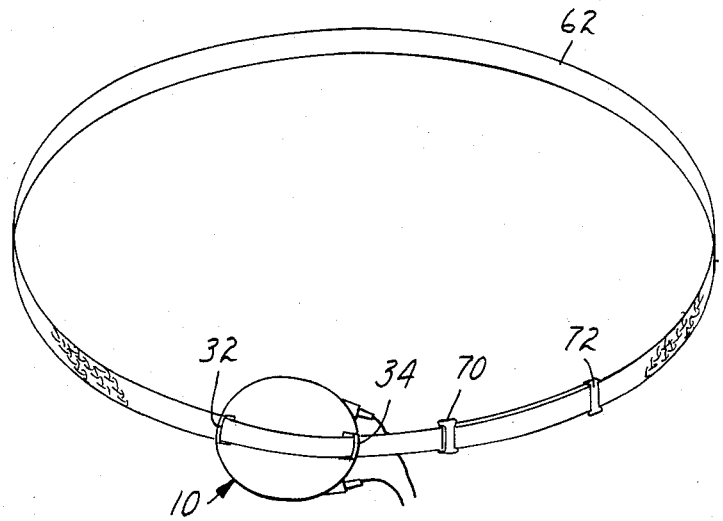

Two examples of waist attachments are illustrated in FIGS. 6 and 7. In FIG. 6 the stimulator 10 is secured to a belt 62 by hook-and-loop strap 64 passing through first attachment point 32 and second attachment point 34. The belt 62 is secured around the waist of the wearer by a hook-and-loop fastener portion 66 fed through a D-ring 68. FIG. 7 shows a similar arrangement in which the stimulator 10 is secured to belt 62 by having belt pass through first attachment point 32 and second attachment point 34. Belt 62 is secured around the waist by a swimsuit closure hook 70. Belt 62 may be adjusted by a slide 72. It is preferred that the belt 62 be constructed from an approximately one-half inch stretch soft bra strap material.

Thus there has been shown and described a transcutaneous electrical nerve stimulator which reflects fundamental human factors research into a new application area for transcutaneous electrical nerve stimulation devices. It is to be recognized and understood, however, that various changes, modifications and substitutions in the form and in the details of the present invention may be made by those skilled in the art without departing from the scope of the following claims.

We claim:

1. A transcutaneous electrical nerve stimulator comprising:
   electrical means for generating and controlling a predetermined set of electrical stimulus signals which are adapted to be applied to a body;
   a housing containing said electrical means, said housing being of a generally flattened convex disk shape with well-rounded edges;
   a first switch means mounted on a side edge of said housing and coupled to said electrical means said first switch means for controlling the intensity of one of said set of electrical stimulus signals; and
   a second switch means mounted on a side edge of said housing and coupled to said electrical means, said second switch means for controlling the power of said electrical means.

2. A transcutaneous electrical nerve stimulator as in claim 1 wherein said electrical means includes means for generating one of said set of electrical stimulus signals with an amplitude which may be varied and wherein said first switch means includes rocker switch means for increasing said amplitude when said rocker switch means is pushed by an operator in a first direction and decreasing said amplitude when said rocker switch means is pushed by an operator in the opposite direction.

3. A transcutaneous electrical nerve stimulator as in claim 2 wherein said electrical means includes a plurality of independent stimulation channels each generating a predetermined set of electrical stimulus signals, wherein said first switch means controls one of said set of electrical stimulus signals of one of said plurality of independent stimulation channels and which further comprises at least one further rocker switch means mounted on an edge of said housing and coupled to said electrical means for controlling the amplitude of one of said set of electrical stimulus signals of another of said plurality of stimulation channels in a manner similar to the manner in which said first rocker switch means controls the amplitude of its associated one of said set of electrical stimulus signals.

4. A transcutaneous electrical nerve stimulator as in claim 3 wherein said housing is divided into two lateral hemispheres said first switch means and said further switch means are mounted on the side edge of one of said two lateral hemispheres of said housing.

5. A transcutaneous electrical nerve stimulator as in claim 2 wherein said second switch means is a slide switch and wherein said first switch means and said second switch means are mounted on opposite side edges of said housing.

6. A transcutaneous electrical nerve stimulator as in claim 2 wherein said first switch means includes means for changing said amplitude by one of a plurality of discrete steps when pushed momentarily and changing said amplitude sequentially through said plurality of said discrete steps when pushed continuously for at least one half-second.

7. A transcutaneous electrical nerve stimulator as in claim 1 wherein said housing is of a slightly elliptical shape.

8. A transcutaneous electrical nerve stimulator as in claim 7 wherein said housing has a first strap attachment point along said side edge of said flattened disk.

9. A transcutaneous electrical nerve stimulator as in claim 8 wherein said housing has a second strap attachment point along said side edge of said flattened disk opposite said first strap attachment point.

10. A transcutaneous electrical nerve stimulator as in claim 9 wherein said housing has a tapered depression at said first strap attachment point and said second strap attachment point.

* * * * *